United States Patent [19]
Saitoh

[11] Patent Number: 5,371,342
[45] Date of Patent: Dec. 6, 1994

[54] ELECTROMAGNETIC-WAVE-OPERATED HEATING APPARATUS HAVING AN ELECTRIC FIELD CONCENTRATING MEMBER

[76] Inventor: Yoshiaki Saitoh, No. 8050 RA-101, Igarashinino-cho, Niigata-shi, Niigata, Japan

[21] Appl. No.: 145,661

[22] Filed: Nov. 4, 1993

Related U.S. Application Data

[63] Continuation of Ser. No. 706,446, May 28, 1991, abandoned.

[30] Foreign Application Priority Data

Jun. 1, 1990 [JP] Japan .................. 2-144818

[51] Int. Cl.⁵ .................................. H05B 6/80
[52] U.S. Cl. ........................ 219/693; 219/696; 219/745; 219/750; 607/101; 607/115; 607/156
[58] Field of Search .......... 219/10.55 A, 10.55 F, 219/10.55 R, 690, 693, 696, 745, 748, 749, 750, 762; 128/804, 783, 784, 790, 799; 600/9, 10, 13, 14; 606/33; 607/100, 101, 102, 103, 115, 147, 154, 156

[56] References Cited

U.S. PATENT DOCUMENTS

| | | | |
|---|---|---|---|
| 3,397,296 | 8/1968 | Curran | 219/10.55 F |
| 3,555,232 | 1/1971 | Bleackley | 219/10.55 A |
| 3,784,777 | 1/1974 | Soulier | 219/10.55 A |
| 3,934,106 | 1/1976 | MacMaster et al. | 219/10.55 F |
| 4,140,130 | 2/1979 | Storm, III | 128/404 |
| 4,144,434 | 3/1979 | Chiron et al. | 219/10.55 F |
| 4,378,806 | 4/1983 | Henley-Cohn | 128/804 |
| 4,889,966 | 12/1989 | Meredith | 219/10.55 F |

FOREIGN PATENT DOCUMENTS 0383334  8/1990  European Pat. Off. .
1-209073 8/1989  Japan .

*Primary Examiner*—Philip H. Leung
*Attorney, Agent, or Firm*—Fish & Richardson

[57] ABSTRACT

In an electromagnetic-wave-operated heating apparatus in which, with a body to be heated such as a living body inserted into the cavity resonator incorporating at least one reentrant, an electromagnetic wave produced by high frequency energy supplied into the cavity resonator is used to heat the body; an electric field concentrating member is provided between the reentrant and the body in such a manner that the electric field concentrating member is provided to be electrically disconnected to the reentrant, whereby, under an ordinary condition that the body held in the apparatus is not in parallel with the end face of the reentrant, a deep portion of the body can be heated with high efficiency.

36 Claims, 6 Drawing Sheets

ELECTROMAGNETIC-WAVE-OPERATED HEATING APPARATUS HAVING AN ELECTRIC FIELD CONCENTRATING MEMBER

This application is a continuation of U.S. patent application Ser. No. 07/706,446 filed May 28, 1991, now abandoned.

BACKGROUND OF THE INVENTION

This invention relates to an electromagnetic-wave-operated heating apparatus in which high frequency energy is supplied to a three-dimensional resonator to produce an electric field thereby to heat a local portion of a body.

Figure 14:
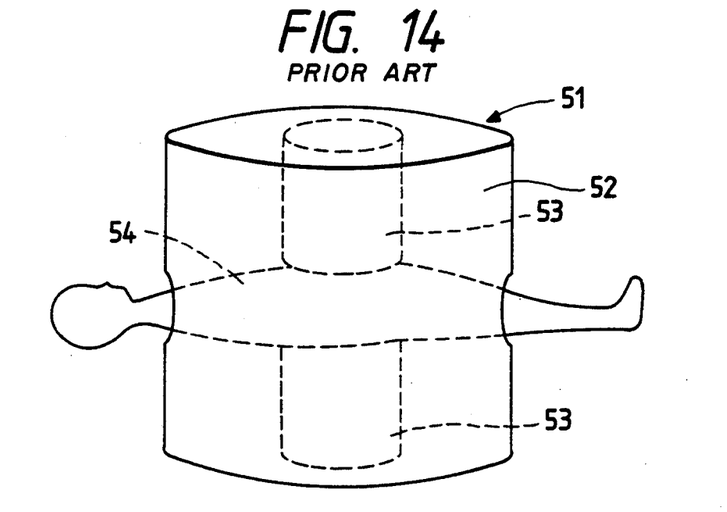
FIG. 14 is a perspective view showing a conventional electromagnetic-wave-operated heating apparatus.
Figure 15:
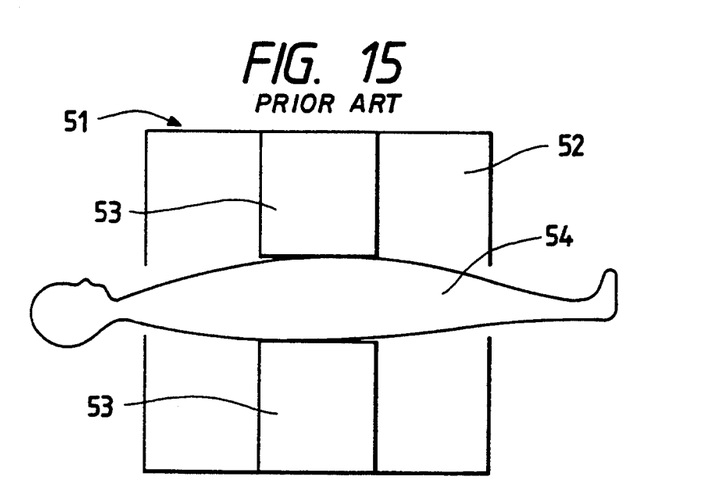
FIG. 15 is a vertical sectional view of the conventional apparatus shown in FIG. 14.

In a conventional electromagnetic-wave-operated heating apparatus, as shown in FIGS. 14 and 15, in the cavity 52 of a three-dimensional resonator 51 internal electrodes 53 are formed by depressing part of the cavity 52 or by using conductors to provide a concentrated electric field for heating (cf. Japanese Patent Application (OPI) No. 209073/1989 (the term "OPI" as used herein means an "unexamined published application")).

In the conventional apparatus, high frequency energy is applied to the three-dimensional resonator 51 to cause resonance in the cavity 52, which causes a strong electric field E to be formed between the internal electrodes and the conductor of the cavity 52 confronted therewith, while a strong magnetic field H is produced which surrounds the electric field E. The electric field E is enclosed by the strong magnetic field H so not to diffuse. A strong electric field is formed, concentrated at the central axis of the internal electrodes 53. With the electromagnetic field thus formed, a desired portion of a body 54 to be heated is heated with high concentration.

However, it has been found through experiments that, with the conventional electromagnetic-wave-operated heating apparatus, the results of heating are not always comparable to those which have been proposed.

As a result, the following facts have been found. When the body to be heated is in contact with the reentrants, the Q (quality factor) of the resonator is lowered, and the resonance frequency cannot be specified, so that it is impossible to heat the body. A gap between the body and the reentrants is needed. Only when the ends of the reentrants are parallel to each other, and the body to be heated is parallel to the ends of the reentrants can a deep local portion of the body be heated. However, in practice, these special conditions are rarely satisfied; the body to be heated is often not quite parallel or uneven. Thus, it is impossible to heat a local portion of the body with high concentration.

SUMMARY OF THE INVENTION

Accordingly, an object of this invention is to eliminate the above-described difficulties accompanying a conventional electromagnetic-wave-operated heating apparatus.

More specifically, an object of the invention is to provide an electromagnetic-wave-operated heating apparatus with which, under the ordinary condition that the body to be heated is not completely parallel, a deep local portion of the body can be heated.

The foregoing objects and other object of the invention have been achieved by providing an electromagnetic-wave-operated heating apparatus where at least one reentrant is provided in a cavity resonator, and with a body to be heated such as a living body or an object inserted into the cavity resonator, an electromagnetic wave produced by high frequency energy supplied to the cavity resonator is used to heat the body. According to the invention, an electric field concentrating member is provided between the reentrant and the body so that the electric field concentrating member is not electrically connected to the reentrant.

In the apparatus, the heating electric field is concentrated by the electric field concentrating member, so that a deep portion of the body is heated with high efficiency.

The nature, principle and utility of the invention will become more apparent from the following detailed description when read in conjunction with the accompanying drawings, in which similar parts are designated by similar reference numerals or characters.

DETAILED DESCRIPTION OF THE INVENTION

Preferred embodiments of this invention will be described with reference to the accompanying drawings.

Figure 1:
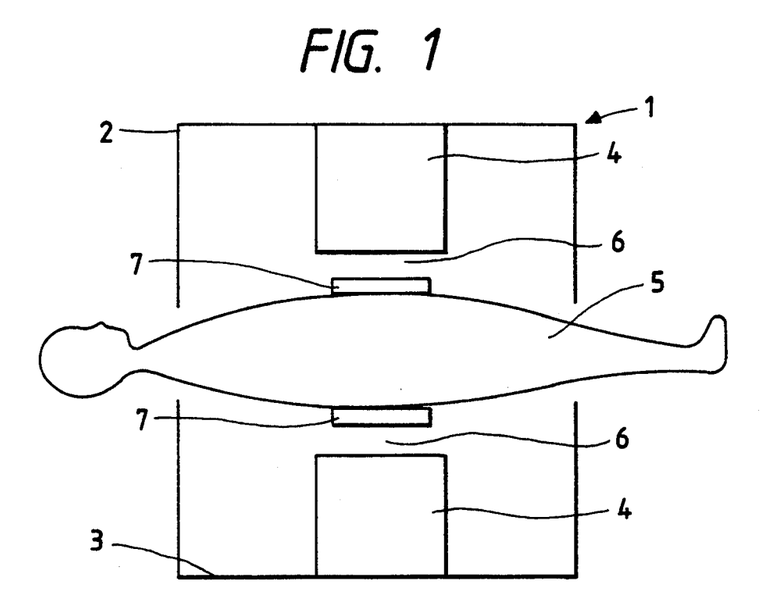
FIG. 1 is a vertical sectional view showing an example of an electromagnetic-wave-operated heating apparatus which constitutes an embodiment of this invention.

An example of an electromagnetic-wave-operated heating apparatus, which constitutes a first embodiment of the invention, is constructed as shown in FIG. 1. That is, a cylindrical cavity resonator 1 has reentrants 4 and 4 inside of it which extend toward each other from the top surface 2 and the bottom surface 3, respectively, and gaps 6 and 6 formed between the body 5 to be heated and the reentrants 4 and 4, respectively. Electric field concentrating members 7 and 7 are placed on the body 5.

In the electromagnetic-wave-operated heating apparatus, the gaps 6 increase the Q (quality factor) of the cavity resonator 1. As a result, the resonance frequency of the cavity resonator can be measured, and the value of a high frequency supplied from an external oscillator (not shown) can be determined. Thus, the body can be effectively heated.

It has been found through experiments that when no electric field concentrating members 7 are used, the following difficulties are involved. The electric field concentrates on parts of the edges of the reentrants 4, and the portions of the body corresponding to the edges are heated greatly. And on the parts of the edges where the electric field concentrates cannot be determined, it is difficult to heat the desired portion of the body.

On the other hand, when the electric field concentrating members 7 are used, the electric field from the reentrants 4 is concentrated on the electric field concentrating members 7, and then applied to the body 5. Since the electric field concentrating members 7 are placed in contact with or near the body 5, the electric field will not diverge. Because a cavity resonator 1 is used, the electric field is condensed by the magnetic field that surrounds the electric field, so that a deep central portion of the body is heated. Through experimentation it has been repeatedly shown that a desired deep portion of the body 5 held between the reentrants is heated to a high temperature.

The electric field concentrating members 7 are made of an electric conductor. Since current flows freely in the electric conductor, the electric field concentrates on the electric field concentrating members 7, which causes a deep portion of the body to be heated effectively.

The electric field concentrating members 7 may be made of a dielectric. A dielectric is more electrically conductive than air. A material having a higher dielectric constant is more electrically conductive. Hence, the electric field can be concentrated on the electric field concentrating member 7 made of dielectric, so that a deep portion of the body can be heated with high efficiency.

Furthermore, the electric field concentrating members 7 may be made of a material which has a higher dielectric constant than the body 5. The conductivity of current in a dielectric is proportional to the dielectric constant thereof. Hence, when the dielectric constant of the electric field concentrating members 7 is made higher than that of the body 5 to be heated, then similar to the case where the electric field concentrating member 7 is made of metal, the electric field concentrating members 7 increased the concentration of the electric field. Thus, a deep portion of the body 5 can be heated more effectively.

In order to prevent the electric field concentrating member 7 or the body 5 to be heated from falling, a material such as a foamed styrene board having a small dielectric constant may be interposed between the lower reentrant 4 and the lower electric field concentrating member 7.

In the electromagnetic-wave-operated heating apparatus thus constructed, the electric field concentrating members 7 may contact the body 5. In this case, the current collected by the electric field concentrating members 7 is directly applied to the body 5, so that it reaches a deep portion of the body without diverging. Thus, the deep portion of the body can be heated with high efficiency.

The electric field concentrating members 7 may each be in the form of a flat plate. The flat plate shaped electric field concentrating members 7 can concentrate the electric field with high efficiency as long as they are made of an electric conductor or dielectric. Hence, in this case also, a deep portion of the body can be heated more sufficiently with high concentration.

Figure 2:
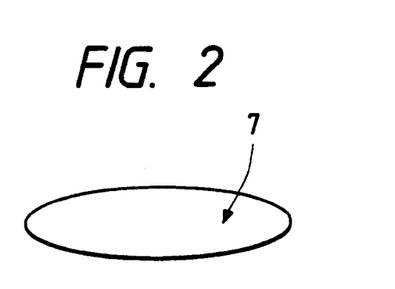
FIGS. 2 through 5 are diagrams showing examples of an electric field concentrating member employed in the apparatus shown in FIG. 1.

The electric field concentrating members 7 may be in the shape of a disk, as shown in FIG. 2. In the use of the disk-shaped electric field concentrating members 7, the electric field concentrates on the central portion of the disk, and accordingly the concentrated heating of a deep portion of the body can be achieved more effectively.

The electric field concentrating members 7 may be shaped so that they are suitable for heating the body. In this case, the electric field is concentrated in the form similar to the configuration of the electric field concentrating members 7. Therefore, the body 5 will be heated in the form in which it is to be heated.

Furthermore, each of the electric field concentrating members 7 may be in the shape of a three-dimensional member having a certain thickness, and is hollow. Even if the electric field concentrating members 7 are hollow, current will flow along the outer surfaces of the electric field concentrating members 7 to the center of its surface confronting with the body 5 to be heated. Thus, the effects of the hollow electric field concentrating members 7 are the same as the solid electric field concentrating members 7. Use of hollow electric field concentrating members 7 contributes to the economical use of material.

In addition, each of the electric field concentrating members 7 may be in the shape of a three-dimensional member which has a certain thickness, and is solid. In this case, the electric field concentrating members 7 may be made of a material uniform in quality. As the thickness of the electric field concentrating members 7 is increased, the distance between the electric field concentrating member 7 and the reentrant 4 is decreased that amount. Accordingly the concentration of the electric field is accelerated as much. Since the electric field concentrating members 7 are solid, current can flow through the inside of the electric field concentrating member to the center of the surface confronting with the body 5 to be heated. Thus, the concentrative heating of a deep portion of the body 5 can be achieved more effectively.

Figure 3:
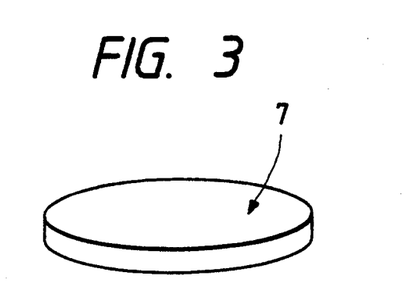
Figure 4:
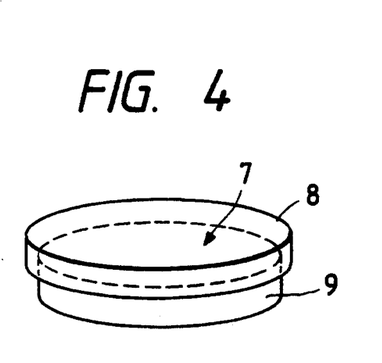
Figure 5:
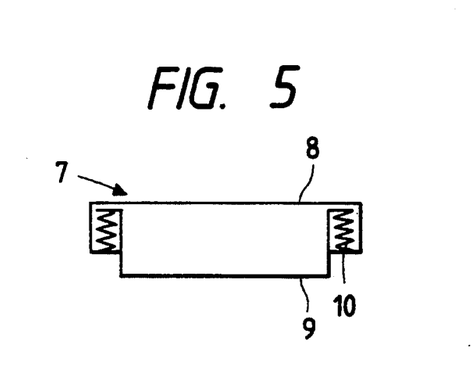

When each of the electric field concentrating members 7 is three-dimensional, it may be cylindrical in shape as shown in FIGS. 3, 4 or 5. In this case, the body 5 is heated in such a manner that the heated portion is circular in the horizontal plane. Being round, the electric field concentrating members 7 have no protrusions, and accordingly the electric field is concentrated on the center. Hence, the concentrative heating of a deep portion of the body 5 can be achieved more effectively.

When each of the electric field concentrating members 7 is three-dimensional, the end portion may have configuration similar to the horizontal section of a portion of the body to be heated. The electric field concentrates in a shape to the configuration of the end portion, and accordingly, the body is heated in the form in which it should be heated.

When the electric field concentrating member 7 is circular as shown in FIGS. 2 and 3, it is preferable that the diameter (d) of the member 7 is at least 1.5 times the thickness (l) of the body 5 to be heated.

Figure 6:
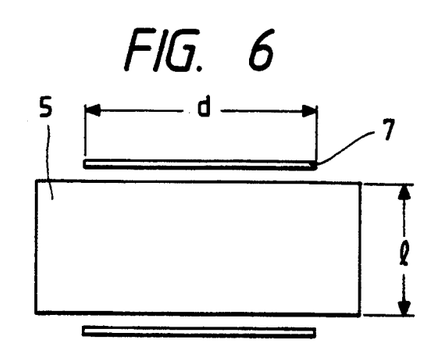
FIG. 6 is an explanatory diagram for a description of a correct relation between the diameter of the electric field concentrating member and the height (thickness) of a body to be heated.

It has been found through experiments that, when the diameter of the electric field concentrating members 7 is small, then concentrated heating of a deep portion of the body 5 cannot be achieved. The electric field collected by the electric field concentrating members 7 diffuses before reaching the deep portion of the body. When the diameter of the electric field concentrating members 7 is large, the electric field will not diffuse, and instead it is condensed by the magnetic field surrounding it. Thus, a deep portion of the body can be heated with high concentration. It has been found through experiments that there is a correction between the diameter of the electric field concentrating members 7 and the thickness of the body 5 to be heated. If the diameter of the electric field concentrating members 7 is at least 1.5 times the thickness of the body 5, then concentrated heating of a deep portion of the body can be accomplished.

As shown in FIG. 4, the electric field concentrating member 7 may be made up of two three-dimensional structures 8 and 9. In this case, the structure 9 is inserted into the structure 8 so that the electric field concentrating member is adjustable in height. Since the height of the electric field concentrating member 7 is adjustable, the resonance frequency of the cavity resonator 1 can be changed. In general, the resonance frequency of the cavity resonator 1 changes with the height of the body 5 to be heated, and therefore it is necessary to change the frequency of the power generator (not shown). However, to change the frequency of the power generator to a desired value is not economical because it is expensive. This difficulty can be overcome by accounting for the change in height of the body 5 by changing the thickness (height) of the electric field concentrating members 7. Thus, the resonance frequency of the cavity resonator 1 can be maintained constant at all times. The oscillator is economical and can be manufactured at low cost.

In order that the three-dimensional structures 8 and 9 forming the electric field concentrating member 7 are electrically in contact with each other, it is effective to dispose electrically conductive materials or electrical conductive elastic materials 10 between the three-dimensional structures 8 and 9 as shown in FIG. 5. When the structures 8 and 9 are made of a rigid material, then they are not always in good contact with each other. This difficulty may be overcome by interposing electrically conductive material or electrically conductive springs 10 between the three-dimensional structures 8 and 9. The current flows between the two structures 8 and 9 are sufficient. Hence, concentrated heating of a deep portion of the body 5 can be achieved with high efficiency.

In order that the structures 8 and 9 are held electrically in contact with each other, they may be made of an electrically conductive elastic material. Furthermore, the contact portions of the structures 8 and 9 may be made of an electrically conductive elastic material. The structures 8 and 9 are then electrically in contact with each other, so that current will flow between them, thus reaching the center of the surface which confronts with the body. Thus, a deep portion of the body can be heated with high concentration.

In order to make the structures 8 and 9 electrically conductive, it is effective to interpose dielectric materials or dielectric elastic materials between the contact regions of those structures 8 and 9 as shown in FIG. 5. If the structures 8 and 9 are made of a rigid material, then they are not always held in good contact with each other. This difficulty may be overcome by interposing the dielectric materials or dielectric elastic materials between the three-dimensional structures 8 and 9. In this case, current flows between the structures 8 and 9 satisfactorily, as a result of which the concentrative heating of a deep portion of the body can be achieved more effectively.

In order that the structures 8 and 9 are held electrically in contact with each other, they may be made of a dielectric elastic material. Furthermore, for the same purpose, the contact portions of the structures 8 and 9 may be made of a dielectric elastic material. The structures 8 and 9 are then electrically in contact with each other, so that current will flow between them sufficiently, thus reaching the center of the surface which confronts with the body. Thus, the effect that a deep portion of the body is heated with high concentration is obtained sufficiently.

Figure 7:
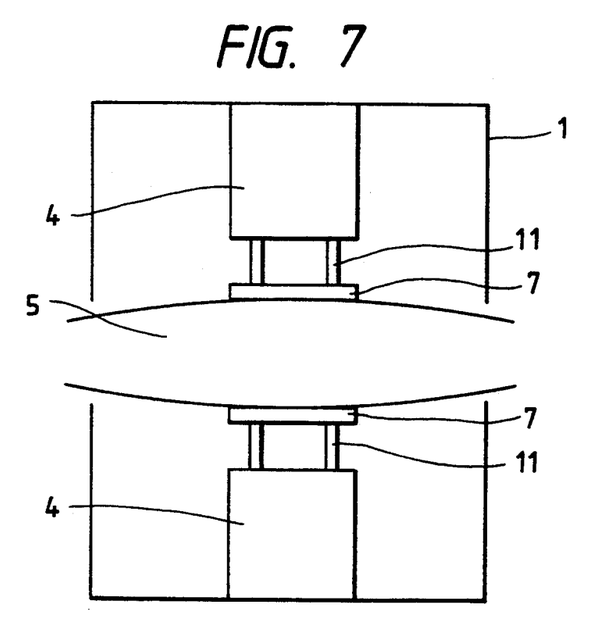
FIGS. 7 through 10 are diagrams showing examples of a method of fixing the electric field concentrating member.

The electric field concentrating members 7 are supported as shown in FIG. 7. The members 7 are secured through insulators 11 to the reentrants 4, respectively. With the electric field concentrating members 7 placed on the body 5 to be heated, the concentration of electric field is effected. However, when the electric field concentrating members 7 are pushed against the body 5 to be heated, the concentration of electric field is accelerated, Hence, the apparatus should be designed so that the electric field concentrating members 7 are secured to the reentrants 4 by the insulators 11 whereby pressure is applied to the electric field concentrating members 7.

Figure 8:
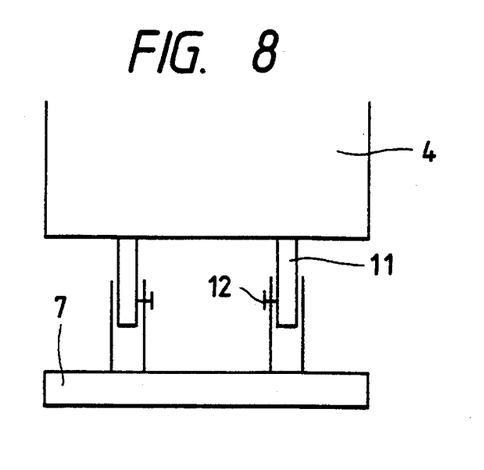

The length of the insulators 11 for securing the electric field concentrating members 7 may be made variable by means of screws 12, as shown in FIG. 8, so that the contact between the electric field concentrating members 7 and the body 5 to be heated is adjustable. For the above-described reason, the electric field concentrating members are secured in the above-described manner. However, if the pressure is excessively high, then it may adversely affect the body 5 to be heated. Therefore, the length of the insulators 11 is adjusted so that the most suitable pressure is applied to the body 5 to be heated.

Figure 9:
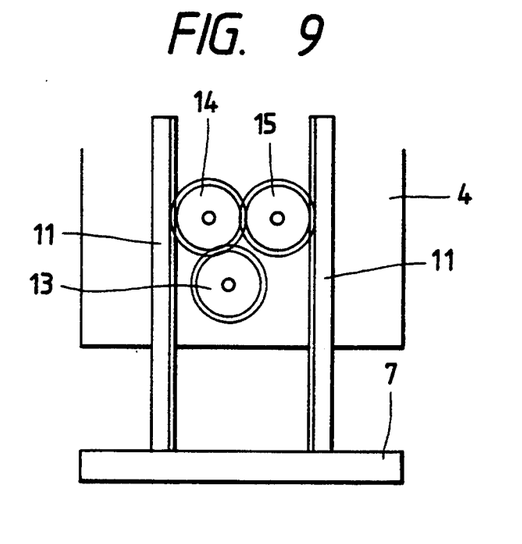

As shown in FIG. 9, an electric motor may be provided inside the reentrant. The motor is used to drive gears 13, 14 and 15 successively, or to drive gear 14 directly to drive a rack formed on the insulators 11 to move the insulators 11 back and forth so that the contact between the electric field concentrating members 7 and the body 5 to be heated is adjustable. That is, by controlling the motor, the most suitable pressure can be obtained for the body 5 to be heated.

Figure 10:
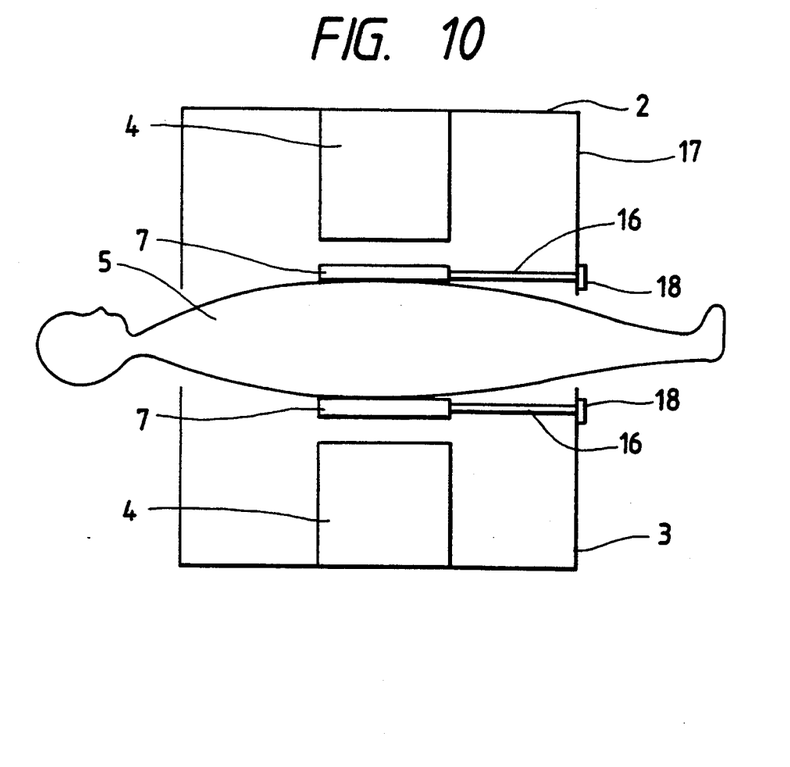

The electric field concentrating members 7 may be secured to the wall 17 (or the top 2 or the bottom 3) of the cavity resonator 1 through insulators 16 as shown in FIG. 10. For the same reason as described above, with the electric field concentrating members 7 secured in the above-described manner, the electric field can be concentrated more effectively.

In FIG. 10, the insulators 16 for securing the electric field concentrating members 7 are movable on the wall 17 of the cavity resonator 1. The insulators 16 are fixedly secured to the wall 17 with fixing members 18 so that the contact between the electric field concentrating members 7 and the body 5 to be heated is best. In this case, the pressure applied to the body 5 to be heated can be changed to a desired value.

It is preferable that the two electric field concentrating members 7 are secured so that their surfaces oppose each other in parallel, as shown in FIG. 7.

When the two surfaces of the electric field concentrating members 7 that oppose each other are large and are not in parallel, then the electric field concentrates on the parts of the electric field concentrating members 7 which are spatially closest, and accordingly the parts are locally heated (such a condition is necessary as the case may be, and therefore in such as case, the electric field concentrating members are intentionally not in parallel). In general, this phenomenon is against the object of heating the body. Hence, the electric field concentrating members 7 are so secured that the two opposing surfaces are as parallel to each other as possible.

When only one electric field concentrating member is used, it should be secured so that its surface is in parallel to the surface of the reentrant which is opposite it.

Figure 11:
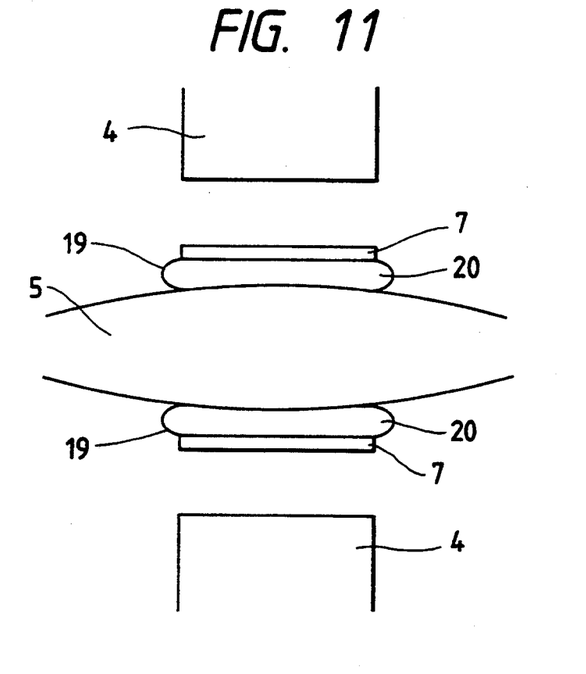
FIG. 11 is a vertical sectional view showing another example of the electromagnetic-wave-operated heating apparatus which constitutes another embodiment of the invention.

FIG. 11 shows another example of the electromagnetic-wave-operated heating apparatus which constitutes a second embodiment of the invention. In the apparatus, bags 19 and 19 are disposed between the body 5 to be heated and the electric field concentrating members 7 and 7, respectively. The bags 19 contain a solution 20.

The electric field concentrating members 7 are fixedly secured in so that they are in parallel with each other. Even when the electric field concentrating members 7 are held in contact with the body 5 to be heated, the contact is poor if the surfaces of the body 5 are not flat. The area of contact is not large enough, and accordingly, sufficient current will not flow into the body 5 through the electric field concentrating members 7. In order to overcome this difficulty, the bags 9 are interposed between the body 5 and the electric field concentrating members 7 and 7, respectively, and then solution 20 is injected into the bags 9. With the bags interposed in this manner, the bags 19 are in contact with the body 5 to be heated; thus, the total area of contact is large enough. As a result, a deep portion of the body can be heated with high concentration, and the bags provide a cooling effect on the surface of the body 5.

Figure 12:
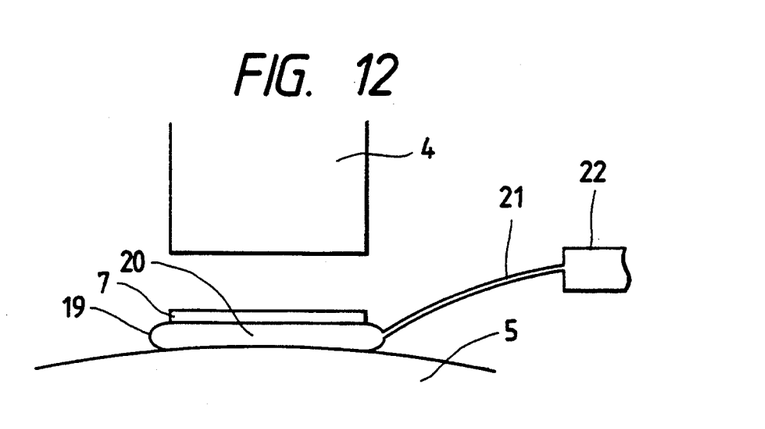
FIGS. 12 and 13 are diagrams showing modifications of the apparatus as shown in FIG. 11.

The above-described apparatus may be modified as shown in FIG. 12. Each of the bags 19 is connected through a pipe 21 to a solution reservoir 22. The height of the bag is changed, or the pressure applied to the surface of the solution in the reservoir is changed to adjust the amount of solution in the bag 19 to adjust the contact between the bag and the body 5 to be heated and to adjust the resonant frequency of the cavity resonator 1. By adjusting the amount of solution in the bag 19, the thickness of the bag is adjusted, whereby the contact between the bag 19 and the body 5 is adjusted, while the resonant frequency of the cavity resonator 1 is changed. That is, the resonant frequency of the cavity resonator 1 is decreased by increasing the thickness of the bag 19, and increased by decreasing the thickness of the bag 19. Hence, the resonant frequency of the cavity resonator 1 can be adjusted to a desired value by adjusting the quantity of solution in the bag.

Figure 13:
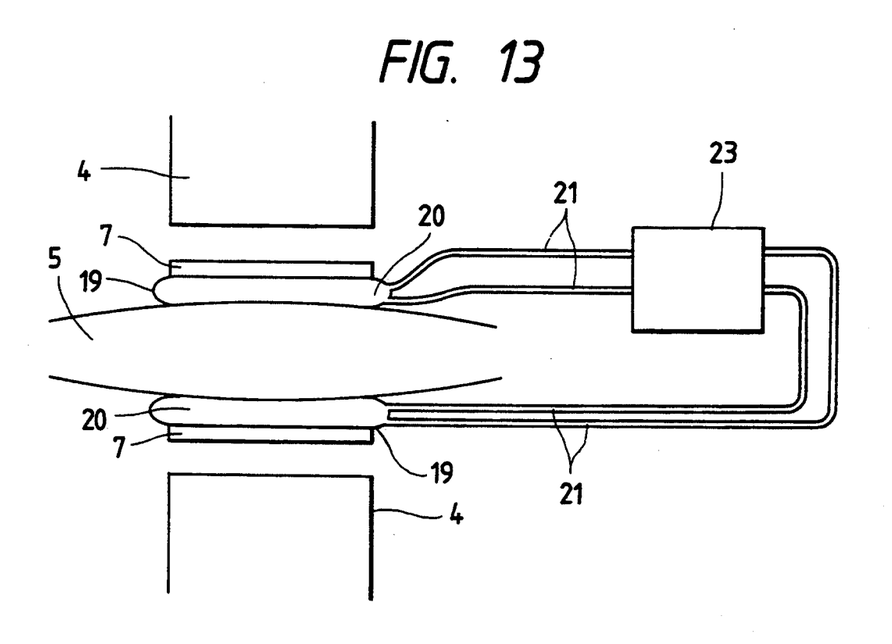

FIG. 13 shows another modification of the electromagnetic-wave-operated heating apparatus, which is so designed as to cool the surface of the body 5. The solution 20 in the bags 19 is circulated through pipes 21 and external cooling unit 23 to cool the surface of the body 5. With the apparatus, the surface of the body can be cooled by cooling the solution 20 which is supplied into the bags. For this purpose, the solution 20 is circulated through the external cooling unit 23 so that it maintains a low temperature at all times, and accordingly the surface of the body is cooled by thermal conduction.

The solution 20 in the bags 19 may dielectric. The bags 19 are interposed between the body 5 and the electric field concentrating members 7 and 7, respectively, as described above, and a solution 20, having the same dielectric constant as the body 5, is supplied to the bags 19. In this case, even if the body 5 is not parallel to the reentrants, the body 5 is parallel therewith. Thus, a deep portion of the body can be heated effectively.

It is preferable that the dielectric supplied to the bags 19 has a larger dielectric constant than the body 5 to be heated. Current will flow in a substance in proportion to its dielectric constant. Hence, when a solution 20 having a higher dielectric constant than the body 5 is supplied to the bags 19, the resistance of the bags 19 against the flow of current is decreased, so that the current will flow into the body more effectively. Thus, a deep portion of the body can be heated with high efficiency.

In the above-described apparatus, the electric field concentrating members 7 coupled to, in contact with, or set near the above-described bags 19 may be any of those shown in FIGS. 2 through 6, or they may be eliminated, or may be used instead of the electric field concentrating members 7 flat plates (whose material is not specified). The electric field concentrating members 7 may be secured according to any of the methods described with reference to FIGS. 7 through 9, or according to any of the methods in combination. It is obvious that any of the electric field concentrating members 7 shown in FIGS. 2 through 6 function satisfactorily. When the electric field concentrating members 7 are merely coupled to the bags 19, sometimes the two electric field concentrating members 7 may not be held in parallel with each other, or the body 5 to be heated may be moved. In order to eliminate these difficulties, the electric field concentrating members 7 are secured according to any of the methods described with reference to FIGS. 7 through 9, or according to any of the methods in combination.

The technical concepts of the above-described embodiments can be applied to an electromagnetic-wave-operated heating apparatus in which the reentrants 4 are not in contact with the top 2 and the bottom 3 of the cavity resonator 1.

As described above, in the electromagnetic-wave-operated heating apparatus of the invention, the electric field concentrating members 7 are provided between the body to be heated and the reentrants so that the reentrants are not in contact with the body. Therefore, the heating electric field applied from the reentrants to the body to be heated is concentrated by the electric field concentrating members 7, thus heating a deep portion of the body with high efficiency.

While the invention has been described in connection with the preferred embodiments, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. An electromagnetic-wave-operated heating apparatus for heating a body, comprising:
   a cavity resonator defining a first cavity for receiving a body therein, said cavity resonator including a pair of opposing reentrants for generating an electromagnetic wave within said first cavity;
   an electric field concentrating member disposed between said reentrants and provided adjacent to and spaced from one of said reentrants, so that said electric field concentrating member is electrically isolated from said reentrants, wherein said electric field concentrating member and an end of one of said reentrants define a second cavity therebetween, and a side of said electric field concentrating member facing said one reentrant is planar;

a support member attached to said electric field concentrating member and within said first cavity; and means for moving said support member relative to the ends of said reentrants to adjust the position of said electric field concentrating member.

2. An apparatus as claimed in claim 1, in which said electric field concentrating member is made of an electric conductor.

3. An apparatus as claimed in claim 1, in which said electric field concentrating member is made of a dielectric.

4. An apparatus as claimed in claim 3, in which said dielectric forming said electric field concentrating member is larger in dielectric constant than said body to be heated.

5. An apparatus as claimed in claim 1, in which said electric field concentrating member is in the form of a flat plate.

6. An apparatus as claimed in claim 1, in which said electric field concentrating member is circular.

7. An apparatus as claimed in claim 6, in which the diameter of the body to be heated is at least 1.5 times the thickness of said electric field concentrating member.

8. An apparatus as claimed in claim 1, in which said electric field concentrating member is shaped in compliance with the configuration of a portion of said body which is to be heated.

9. An apparatus as claimed in claim 1, in which said electric field concentrating member defines a cavity therein.

10. An apparatus as claimed in claim 9, in which said cavity in said electric field concentrating member is filled with a material.

11. An apparatus as claimed in any of claims 9 and 10, in which said electric field concentrating member is cylindrical.

12. An apparatus as claimed in any of claims 9 and 10, in which the surface of said electric field concentrating member which confronts with said body to be heated is shaped in compliance with the configuration of a portion of said body which is to be heated.

13. An apparatus as claimed in claim 1, in which said electric field concentrating member comprises two cup-shaped members which are fitted together in such a manner that one of said cup-shaped members is inserted into the other.

14. An apparatus as claimed in claim 13, in which contact members which are made of an electrically conductive material are interposed between engaging surfaces of said two cup-shaped members in such a manner that said two cup-shaped members are electrically connected to each other.

15. An apparatus as claimed in claim 13, in which contract members which are made of a dielectric material are interposed between engaging surfaces of said two cup-shaped members.

16. An apparatus as claimed in claim 1, in which the length of an insulator adapted to fixedly secure said support of said electric field concentrating member is adjusted by means of an electric motor, to adjust the condition of contact of said electric field concentrating member with said body to be heated.

17. An apparatus as claimed in claim 1, in which said electric field concentrating member is supported through an insulator on a wall of said cavity resonator.

18. An apparatus as claimed in claim 1, in which an insulator adapted to secure said electric field concentrating member is movable on a wall of said cavity resonator, said insulator being moved to adjust the condition of contact of said electric field concentrating member with said body to be heated.

19. An apparatus as claimed in claim 1, in which two electric field concentrating members are provided in said cavity resonator in such a manner that the opposing surfaces thereof are in parallel with each other.

20. An apparatus as claimed in claim 1, in which said electric field concentrating member is disposed within said cavity resonator in such a manner that a surface thereof which is adjacent said body is in parallel with an end face of said one reentrant.

21. An apparatus as claimed in claim 1, in which a bag is interposed between said electric field concentrating member and said body to be heated, said bag containing a solution.

22. An apparatus as claimed in claim 21, which comprises means for adjusting the quantity of solution in said bag.

23. An apparatus as claimed in claim 21, which comprises means for circulating the solution contained in said bag.

24. An apparatus as claimed in claim 21, in which said solution is of a dielectric.

25. An apparatus as claimed in claim 24, in which said solution of dielectric is larger in dielectric constant than said body to be heated.

26. An apparatus as claimed in claim 1, in which said electric field concentrating member defines a cavity therein, said electric field concentrating member is cylindrical, and a surface of said electric field concentrating member adjacent said body is shaped in compliance with the configuration of a portion of said body which is to be heated.

27. An apparatus as claimed in claim 26, in which said cavity in said electric field concentrating member is filled with a material.

28. An apparatus as claimed in claim 1, in which the body to be heated defines a cavity therein, said electric field concentrating member is cylindrical, and the diameter of said electric field concentrating member is at least 1.5 times the thickness of said electric field concentrating member.

29. An apparatus as claimed in claim 28, in which said cavity in said electric field concentrating member is filled with a material.

30. An electromagnetic-wave-operated heating apparatus, as claimed in claim 1, wherein said electric field concentrating member comprises a pair of electric field concentrating elements between which said second cavity is defined.

31. An electromagnetic-wave-operated heating apparatus, as claimed in claim 1, wherein said electric field concentrating member comprises a pair of electric field concentrating elements and each of said electric field concentrating elements has a support member attached thereto.

32. An electromagnetic-wave-operated heating apparatus, as claimed in claim 1, wherein said support member is disposed between said electric field concentrating member and the other of said reentrants.

33. An electromagnetic-wave-operated heating apparatus, as claimed in claim 32, wherein said electric field concentrating member comprises a pair of electric field concentrating elements.

34. An electromagnetic-wave-operated heating apparatus, as claimed in claim 32, wherein said support member comprises a pair of support members.

35. An electromagnetic-wave-operated heating apparatus, as claimed in claim 1, wherein one end of said support member is attached to said electric field concentrating member and the other end of said support member is attached to a wall of said first cavity.

36. An electromagnetic-wave-operated heating apparatus, as claimed in claim 35, wherein said electric field concentrating member comprises a pair of electric field concentrating elements.

* * * * *